United States Patent [19]

Kakimoto et al.

[11] Patent Number: 5,352,815
[45] Date of Patent: Oct. 4, 1994

[54] AGENT FOR SUPPRESSION AND INTERCEPTION OF MAILARD REACTION

[75] Inventors: Norihiro Kakimoto, Tokyo; Kunie Nakamura, Kanagawa, both of Japan

[73] Assignee: Asai Germanium Research Institute Co., Ltd., Tokyo, Japan

[21] Appl. No.: 31,997

[22] Filed: Mar. 16, 1993

[30] Foreign Application Priority Data

Mar. 16, 1992 [JP] Japan .................................. 4-091685

[51] Int. Cl.$^5$ .......................... C07F 7/30; A61K 31/28
[52] U.S. Cl. ....................................... 556/83; 556/107
[58] Field of Search ................... 556/83, 107; 514/492

[56] References Cited

U.S. PATENT DOCUMENTS 4,720,564  1/1988  Kakimoto et al. .................... 556/83

FOREIGN PATENT DOCUMENTS 0032485  4/1981  Japan ...................................... 556/83

*Primary Examiner*—José G. Dees
*Assistant Examiner*—Porfirio Nazario-Gonzalez

*Attorney, Agent, or Firm*—Burns, Doane, Swecker & Mathis

[57] ABSTRACT

The present invention provides an agent for suppression or interception of the Mailard reaction, which comprises, as the active component, an organogermanium compound represented by formula (1):

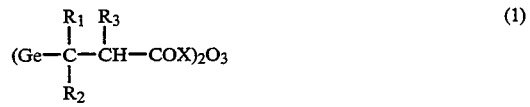

wherein $R_1$ to $R_3$ may be the same or different and each of them represents a hydrogen atom, a lower alkyl group, or a phenyl group; and X represents a hydroxyl group, an O-lower alkyl group, an amino group, or a salt represented by OY (Y is a metal or a basic group-containing compound).

Said agent can effectively suppress or intercept the Mailard reaction and has high safety even when administered for a long period of time.

10 Claims, 6 Drawing Sheets

AGENT FOR SUPPRESSION AND INTERCEPTION OF MAILARD REACTION

FIELD OF THE INVENTION

The present invention relates to an agent for suppression or interception of the Mailard reaction. More particularly, the present invention relates to an agent comprising an organogermanium compound as the active component and having an excellent effect for suppression or interception of the Mailard reaction.

PRIOR ART

The Mailard reaction is a generic name for a series of reactions which start from bonding between saccharide and protein's amino group and end in formation of brown compound. For example, coloring of foods when heated is thought to be a result of the Mailard reaction. The Mailard reaction, which is a non-enzymatic reaction between saccharide and protein, is anticipated to take place also in living bodies, and has come to draw attention recently.

The Mailard reaction proceeds as follows in the initial stage.

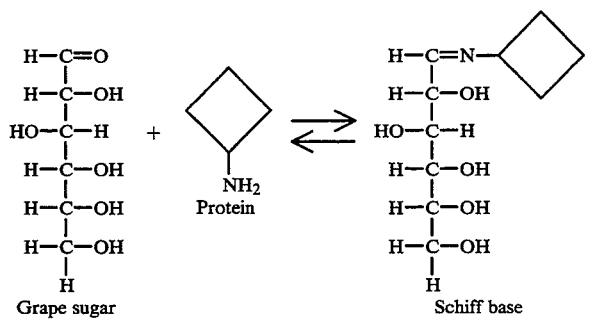

Grape sugar | Schiff base

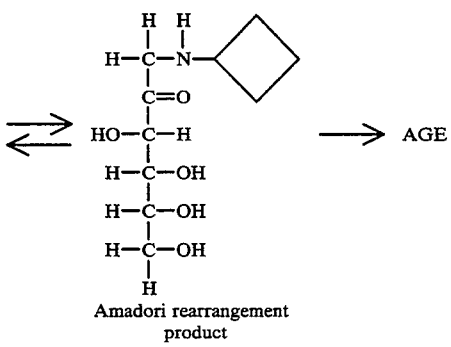

Amadori rearrangement product

→ AGE

The aldehyde group of grape sugar and the amino group of protein bond with each other to form a Schiff base. The Schiff base, which is unstable, quickly gives rise to intramolecular hydrogen rearrangement (Amadori rearrangement) to form an Amadori rearrangement product which is stable as compared with the Schiff base.

In the later stage, the Amadori rearrangement product is converted into a grape sugar derivative via a slow dehydration reaction. The derivative is irreversibly converted into another derivative generically called "AGE" (advanced glycosylation end product). In some cases, the AGE forms a crosslinked product together with another protein. The structures of these derivatives and the crosslinked product are mostly unknown.

It was reported as a result of recent studies that the Amadori rearrangement product had close connection with various diseases, particularly diabetes and aging. For example, Anthony Cerami and Ronald J. Koenig reported that the bloods of diabetic patients examined contained hemoglobin $A_{1C}$ at concentrations higher than those of healthy people and that the concentrations were proportional to the blood sugar levels of said patients. This hemoglobin $A_{1C}$ is an Amadori rearrangement product. Further, a group of Anthony Cerami et al. and other groups detected a number of Amadori rearrangement products in living bodies and reported that diabetic patients examined had Amadori rearrangement products in amounts 2–3 times higher than those of healthy people.

It is anticipated that when a state of high blood sugar lasts long, various proteins in living bodies are converted into respective AGE's and further into crosslinked products owing to the above-mentioned reaction mechanism. This process causes complications of diabetes, owing to a theory. The process also causes even the phenomenon of aging, according to another theory. It was reported that AGE's had actually been accumulated in the duras of diabetes patients and old people.

Hence, it is anticipated that the complications of diabetes and the phenomenon of aging can be suppressed or retarded if an agent is provided which can suppress the Mailard reaction or decompose the compounds formed by the Mailard reaction, such as AGE and the like.

Japanese Patent Application Kokai (Laid-Open) No. 142114/1987 discloses a composition for suppression of protein aging, developed from the above viewpoint, a drug containing said composition, and a method for suppression of protein aging. The method for suppression of protein aging, disclosed in the document comprises administering to a patient an agent having an active nitrogen-containing substituent (e.g. aminoguanidine) and capable of reacting with carbonyl group-containing Mailard reaction products such as Amadori rearrangement product and the like to (1) allow the agent to react with a carbonyl group-containing compound (e.g. Amadori rearrangement product) and thereby (2) prevent their irreversible conversion of the Amadori rearrangement product into a grape sugar derivative and further into AGE, as shown in the following reaction formula.

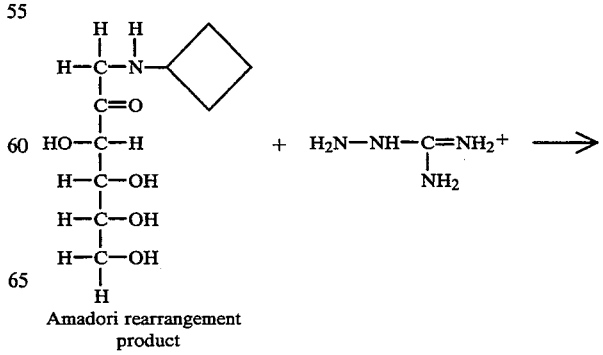

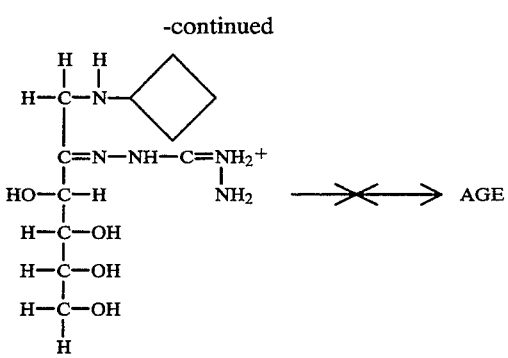

The above reaction mechanism, i.e. the reaction of aminoguanidine or the like with an Amadori rearrangement product to prevent the irreversible conversion of the Amadori rearrangement product into a grape sugar derivative and further into AGE is easy to understand as a chemistry, but the reaction product between aminoguanidine or the like and the Amadori rearrangement product is a protein unexperienced to human bodies and its safety is unknown at all.

When the above agent containing aminoguanidine or the like is administered for the purpose of, for example, suppression of protein aging and treatment of complications of diabetes, the period of the administration is presumed to be very long. Therefore, if the protein formed by the reaction between aminoguanidine and the Amadori rearrangement product has any toxicity, its adverse effect is negligible.

SUMMARY OF THE INVENTION

The present invention has been made under the above situation and is intended to provide an agent which can effectively suppress or intercept the Mailard reaction and which has high safety.

According to the present invention, there is provided an agent for suppression or interception of the Mailard reaction, which comprises, as the active component, an organogermanium compound represented by formula (1):

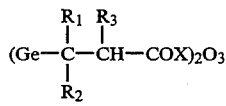 (1)

wherein $R_1$ to $R_3$ may be the same or different and each of them represents a hydrogen atom, a lower alkyl group, or a phenyl group; and X represents a hydroxyl group, an O-lower alkyl group, an amino group, or a salt represented by OY (Y is a metal or a basic group-containing compound).

DETAILED DESCRIPTION OF THE INVENTION

Figure 1:
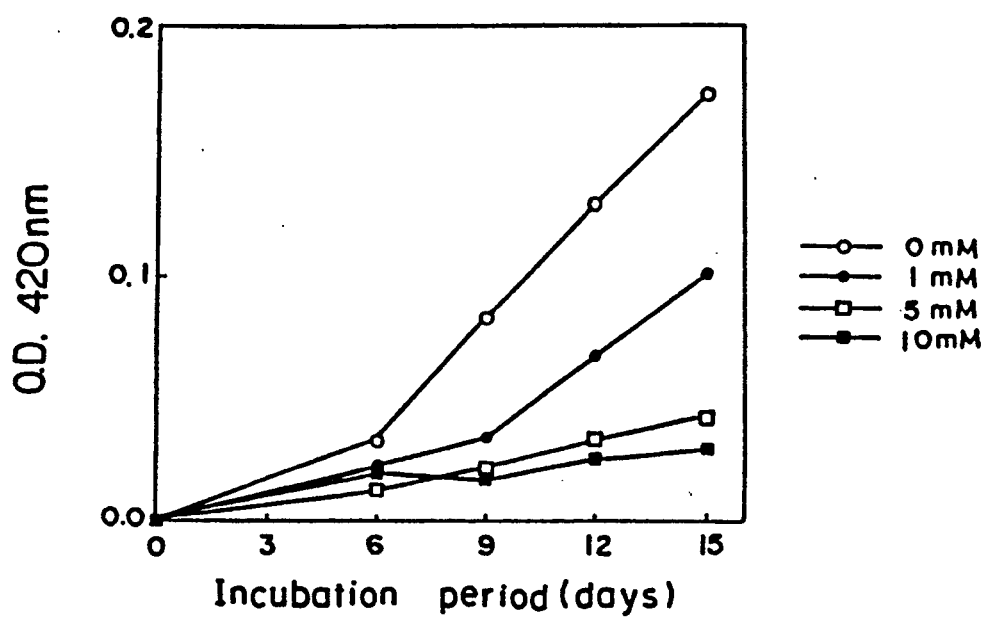
FIG. 1 is a graph showing that the present agent suppresses the formation of AGE.

The present invention is described in detail below.

The agent for suppression or interception of the Mailard reaction according to the present invention comprises, as the active component, an organogermanium compound represented by the above-mentioned formula (1). Description is made first on the compound. In the organogermanium compound of formula (1), the basic skeleton is germylpropionic acid formed by bonding between a germanium atom and a propionic acid derivative having three substituents $R_1$ to $R_3$ and an oxygen-containing group OX, and the germanium atom in the basic skeleton is bonded with oxygen atom at an atomic ratio of 2:3.

In formula (1), $R_1$ to $R_3$ may be the same or different and each of them represents a hydrogen atom, a lower alkyl group such as methyl, ethyl, propyl, butyl or the like, or a phenyl group; and X represents a hydroxyl group, an O-lower alkyl group, an amino group, or a salt represented by OY [Y is a metal such as sodium, potassium or the like (the metal is not being restricted to a monovalent metal)], or a basic group-containing compound such as lysozyme, lysine or the like.

The substituents $R_1$ and $R_2$ are bonded to the α position of the germanium atom and the substituent $R_3$ is bonded to the β position. Therefore, the organogermanium compound usable in the present agent can be exemplified by the following.

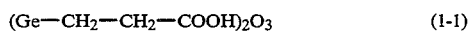 (1-1)

 (1-2)

 (1-3)

 (1-4)

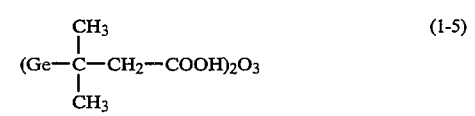 (1-5)

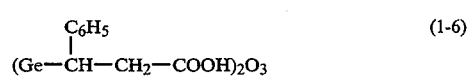 (1-6)

$$(Ge-CH-CH-COOH)_2O_3 \quad \text{with } C_6H_5, CH_3 \text{ substituents} \quad (1\text{-}7)$$

$$(Ge-CH_2-CH_2-COOCH_3)_2O_3 \quad (1\text{-}8)$$

$$(Ge-CH_2-CH_2-CONH_2)_2O_3 \quad (1\text{-}9)$$

$$(Ge-CH_2-CH_2-COO^-Na^+)_2O_3 \quad (1\text{-}10)$$

The organogermanium compounds having the above structures can be produced by various processes.

A compound of formula (1) wherein X=OH, can be produced, for example, by, as shown in the following reaction formula, hydrolyzing a trihalogermylpropionic acid [e.g. trichlorogermylpropionic acid (3)] into which $R_1$ to $R_3$ have been introduced beforehand.

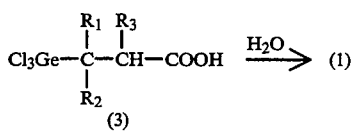

A compound of formula (1) wherein X=an O-lower alkyl group, can be produced, for example, by reacting the above compound (3) with thionyl chloride or the like to convert it into a corresponding acid halide, reacting the acid halide with an alcohol corresponding to the lower alkyl group, and hydrolyzing the reaction product. Further, a compound of formula (1) wherein $X=NH_2$, can be produced, for example, by reacting the acid halide with ammonia.

Furthermore, a compound of formula (1) wherein X is a salt represented by OY and Y is a metal, can be produced by reacting a compound (1) with a metal hydroxide of Y. A compound of formula (1) wherein X is a salt represented by OY and Y is a basic group-containing compound, can be produced by a known acid-base reaction.

The organogermanium compounds obtained as above were measured for nuclear magnetic resonance (NMR) absorption spectrum, infrared (IR) absorption spectrum, etc. The results well support that the compounds are compounds of formula (1).

The formula (1) for the organogermanium compound of the present invention represents the compound in a state of isolated crystals. However, it is known that the compound, when put into water, undergoes hydrolysis at the germanium-oxygen bond and, for example, the compound (1-1) takes the following structure.

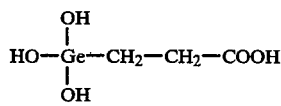

Of the above organogermanium compounds, the compound (1-1) is preferable because it is available rather easily.

The present agent comprising an organogermanium compound of formula (1) as the active component, can be administered by various methods, i.e. orally, parenterally or locally.

The present agent has no restriction with respect to the form, and can be made, as necessary together with a known carrier, etc., into an oral agent (e.g. tablets, powder, capsules), a parenteral agent (e.g. injection) or an agent for local application (e.g. lotion, ointment).

The content of the organogermanium compound (1) in the present agent for suppression or interception of the Mailard reaction varies depending upon the case but is, for example, about 5–500 mg per administration unit. The amount of said compound administered varies depending upon the disease condition but is, for example, about 1–100 mg/kg/day.

The organogermanium compound (1) used in the present agent has very low toxicity. In the case of oral administration of the compound (1-1), the $LD_{50}$ is 6 g or more for mice and 10 g or more for rats.

The present invention is hereinafter described in more detail by way of Examples.

EXAMPLE 1

The organogermanium compound (1-1) was added to a phosphate buffer solution (50 mM, pH 7.4) containing 50 mM of Nα-t-butoxycarbonyl-L-lysine (hereinafter abbreviated to Nα-t-Boc-lysine) as a model protein and 1M of glucose, so that the final concentration became 0, 1, 5 or 10 mM. Then, incubation was conducted at 40° C. for 15 days, after which the formation of AGE was measured by browning degree (absorbance at 420 nm) and the amount of Nα-t-Boc-lysine consumed was measured by high-performance liquid chromatography (hereinafter abbreviated to HPLC) to examine the effect of the organogermanium compound (1-1) added. The results are shown in FIG. 1 and FIG. 2.

Figure 2:
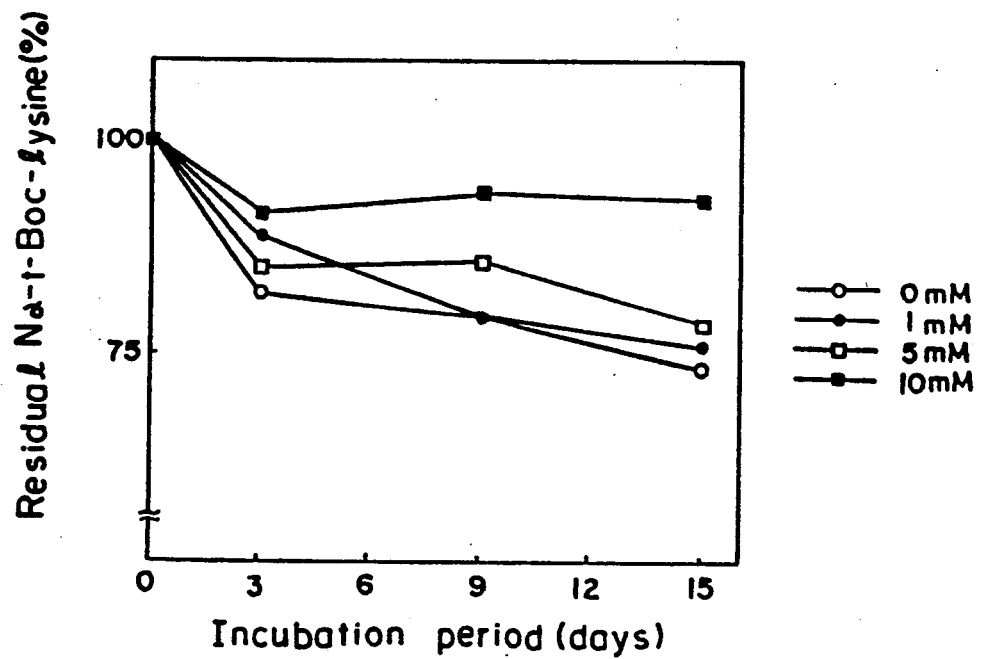
FIG. 2 is a graph showing that the present agent suppresses the consumption of Nα-t-butoxycarbonyl-L-lysine.

As is clear from FIG. 1, the organogermanium compound (1-1) suppressed the formation of AGE dependently upon the concentration of the compound (1-1) and suppressed the formation substantially completely at a concentration of 5–10 mM. A similar trend is seen also in FIG. 2, wherein the organogermanium compound (1-1) suppressed the consumption of Nα-t-Boc-lysine to about 10% at a concentration of 10 mM.

These results indicate that the agent of the present invention has an effect for suppressing the initial stage of the Mailard reaction.

EXAMPLE 2

The organogermanium compound (1-1) was added to a phosphate buffer solution containing 10 mM of Nα-t-butoxycarbonyl-Nε-fructose-L-lysine (hereinafter abbreviated to F-lysine) as a model glycosylated protein, so that the final concentration became 0, 1, 5, 10 or 50 mM. Then, incubation was conducted at 40° C. for 15 days, after which the formation of AGE was measured by browning degree (absorbance at 420 nm) and the amount of F-lysine decomposed was measured by HPLC to examine the effect of the organogermanium compound (1-1) added. The results are shown in FIG. 3 and FIG. 4.

Figure 3:
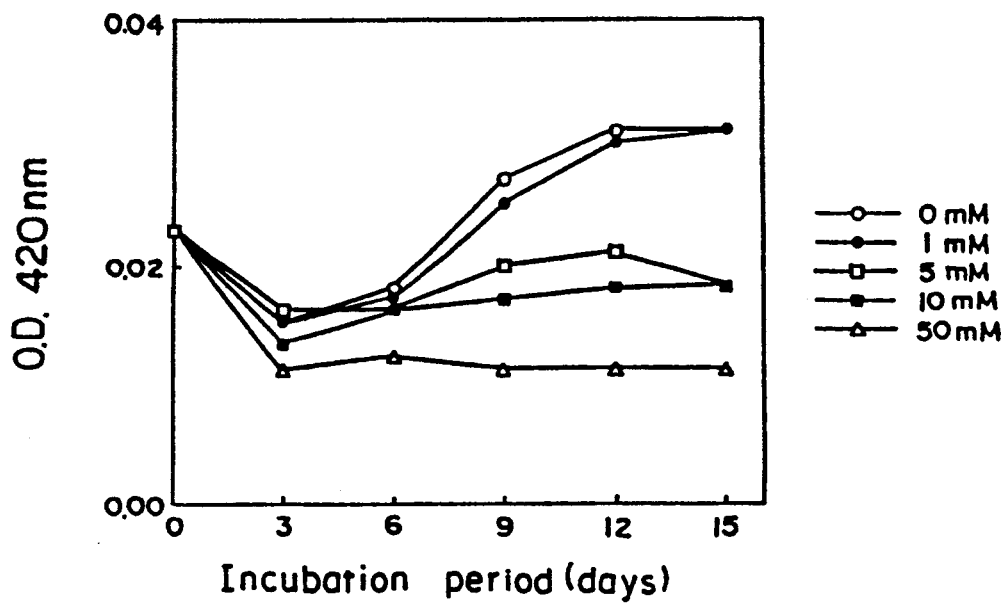
FIG. 3 is a graph showing that the present agent suppresses the formation of AGE from Nα-t-butoxycarbonyl-Nε-fructose-L-lysine.
Figure 4:
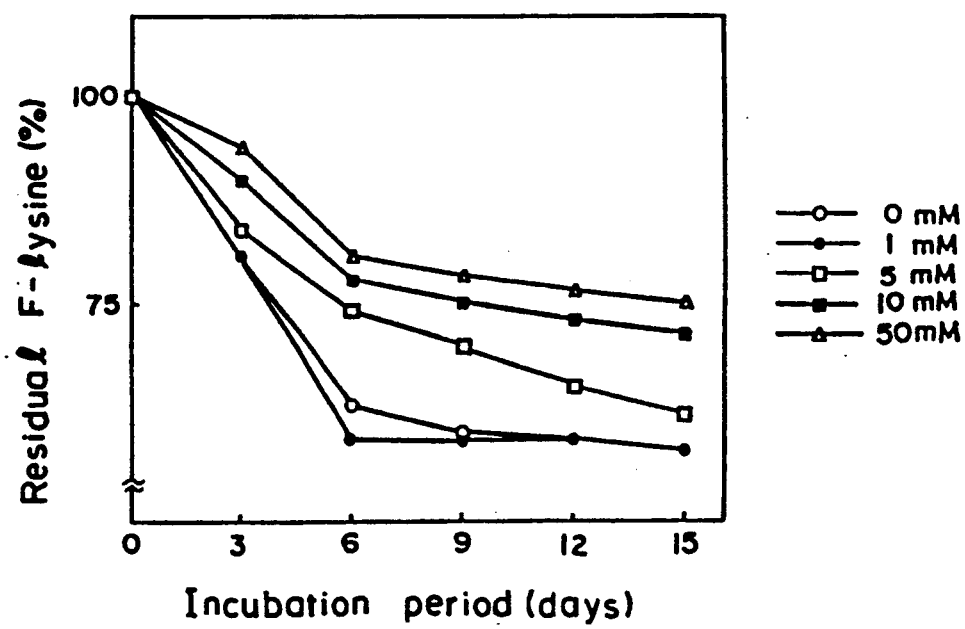
FIG. 4 is a graph showing that the present agent suppresses the decomposition of Nα-t-butoxycarbonyl-Nε-fructose-L-lysine.

As is clear from FIG. 3 and FIG. 4, the organogermanium compound (1-1) suppressed the formation of AGE substantially completely at a concentration of 5–50 mM. As is also clear from FIG. 4, the organogermanium compound (1-1) suppressed the consumption of F-lysine at a concentration of 5–50 mM and suppressed the consumption to about 20% at a concentration of 50 mM.

These results indicate that the agent of the present invention has an effect for suppressing the intermediate or last stage of Mailard reaction.

Incidentally, roughly the same results were obtained also when organogermanium compounds of formula (1)

other than the compound (1-1) were used. However, when aminoguanidine was used in place of the organogermanium compound (1), substantially no effect was obtained.

EXAMPLE 3

20 mg of ribose, 20 mg of alginine and 10 ml of methanol were reacted under refluxing, in a hot bath of 60°–70° C. 10–15 minutes later, 0.1–0.3 ml of acetic acid was added and the reaction was continued for a further 5–10 minutes. Then, the reaction mixture was concentrated under reduced pressure. During the concentration, a small amount of water was added to remove acetic acid. The concentrate was dissolved in 1 ml of water and the solution was subjected to HPLC to collect an Amadori rearrangement product. The product was freeze-dried.

The freeze-dried product of the Amadori rearrangement product was suspended in 4 ml of a sodium phosphate buffer solution (pH 7.4, 0.1M). The suspension was mixed with a sodium phosphate buffer solution containing or not containing 40 mM of the organogermanium compound (1-1), at a 1:1 ratio. The mixture was incubated at 37° C. for 24 hours. Sampling of 0.1 ml was conducted with the lapse of time for immediate analysis by HPLC. When immediate analysis was impossible, the sample was freeze-stored at $-20°$ C.

Figure 5:
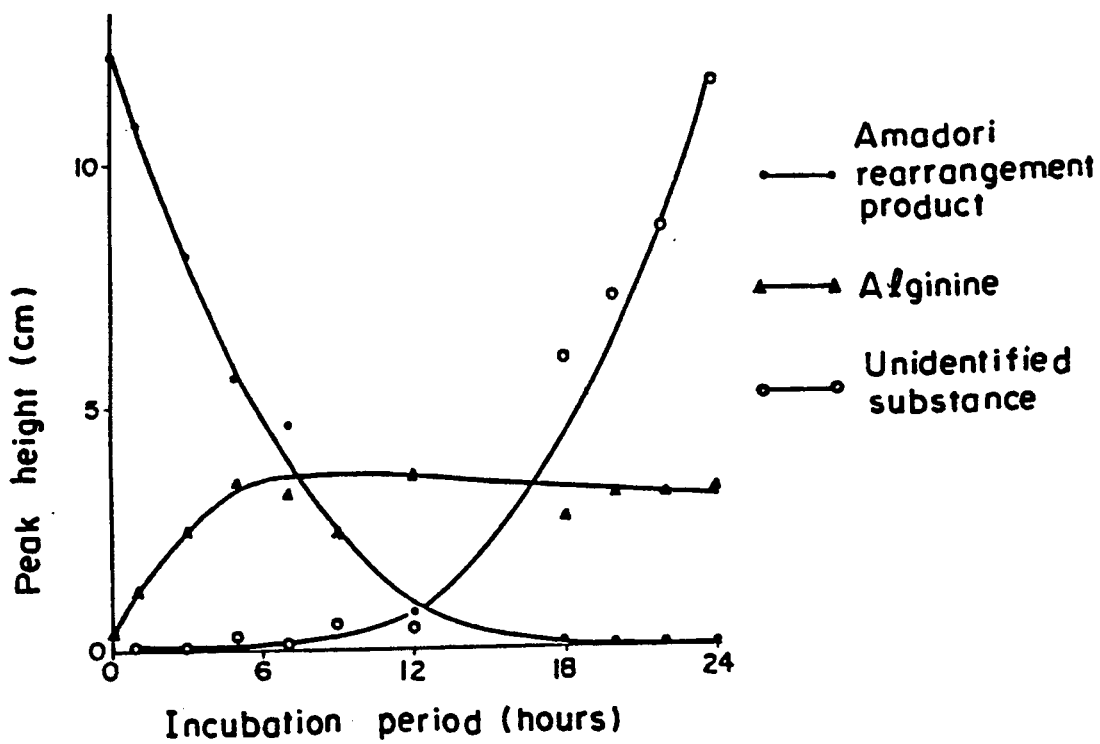
FIG. 5 is a graph showing the decomposition of an Amadori rearrangement product formed from ribose and alginine, when the present agent is not used.
Figure 6:
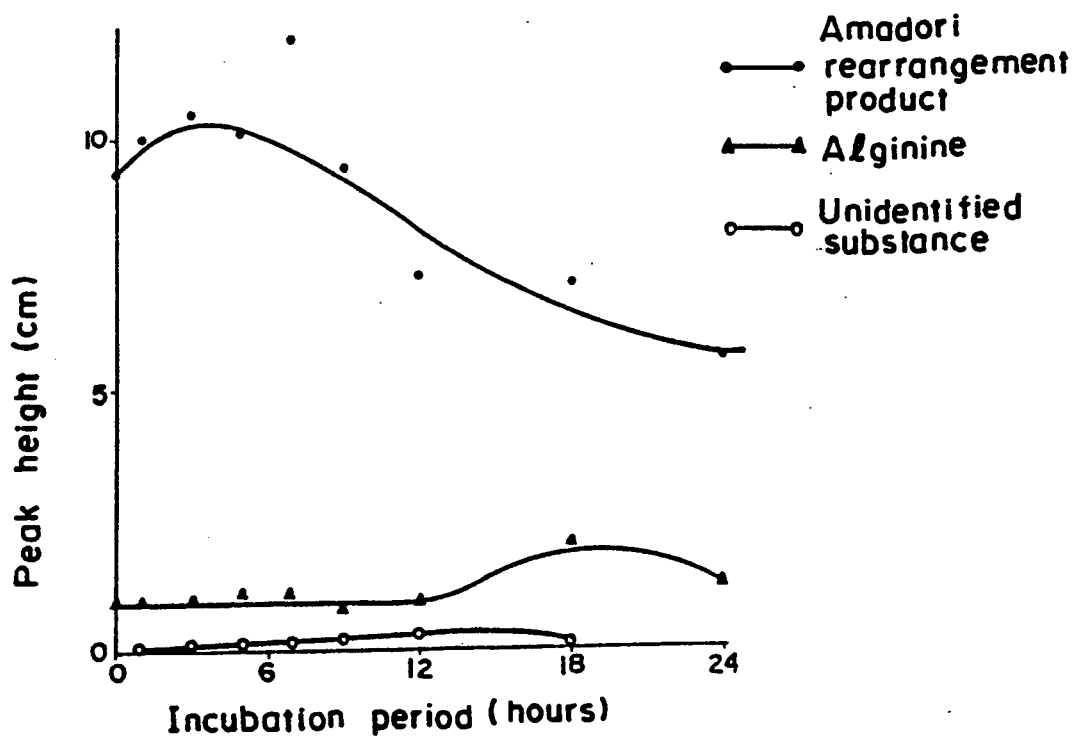
FIG. 6 is a graph showing the decomposition of an Amadori rearrangement product formed from ribose and alginine, when the present agent is used.

When no organogermanium compound (1-1) was added, as shown in FIG. 5, the Amadori rearrangement product disappeared almost completely in 18 hours and alginine increased. In about 11 minutes, an unidentified substance peak appeared and it increased sharply in 9 hours and thereafter. When the organogermanium compound (1-1) was added, however, as shown in FIG. 6, the decrease of the Amadori rearrangement product was very mild and there was substantially seen neither alginine increase nor unidentified substance peak increase.

This indicates that the present agent suppresses the Mailard reaction of a saccharide constituting a nucleic acid such as ribonucleic acid (RNA) or the like.

EXAMPLE 4

Streptozocin was intravenously injected into Sprague-Dawley female rats (total 21 rats each weighing 240–270 g) in an amount of 65 mg per kg of body weight to cause diabetes. Then, the rats were divided into two groups, i.e. a control group and an administered group. An organogermanium compound (1-1) was put into drinking water and orally administered to the administered group at night in an amount of 100 mg per kg of body weight.

4, 8 and 14 weeks after the administration of the organogermanium compound (1-1), blood sampling was made from all the rats of the two groups in hungry state. Each blood taken was measured for blood sugar, glucohemoglobin (hereinafter abbreviated to GHb), glycated albumin (hereinafter abbreviated to GA) and Fructosamine (hereinafter abbreviated to Fru). GHb was measured by affinity chromatography using a mini column, and GA was measured by HPLC using two different columns. The body weight, amount of water taken and amount of food taken, of each rat were also recorded simultaneously.

Figure 7:
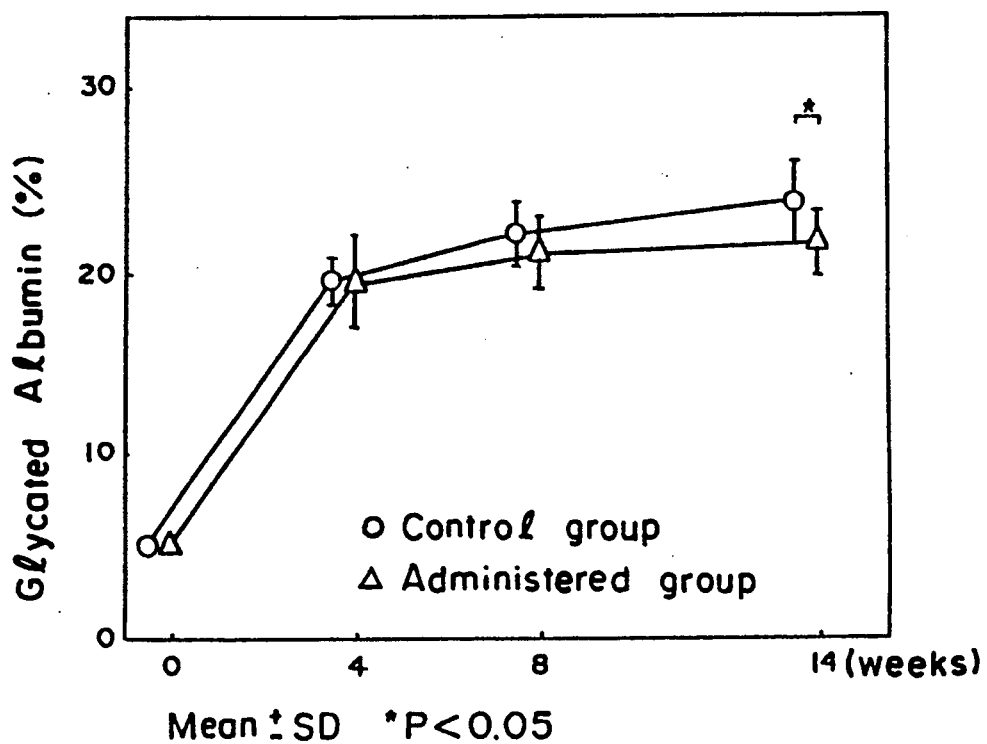
FIG. 7 is a graph showing that the present agent reduces glycated albumin in rats.
Figure 8:
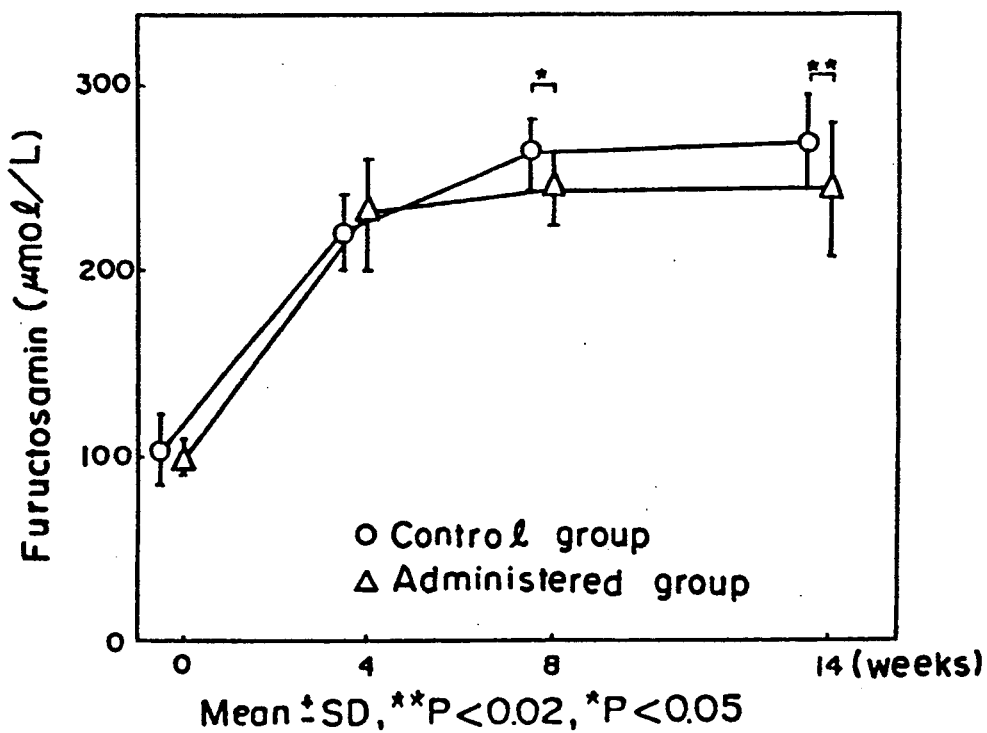
FIG. 8 is a graph showing that the present agent reduces Fructoamine in rats.

GHb was lower in the administered group. Also, GA was significantly lower in the administered group [21.6±1.8% (mean±SD)] in 14 weeks than in the control group (23.8±2.3%), as shown in FIG. 7. At that time, the concentration of albumin in plasma was 1.9±0.3 g/dl in the administered group and 2.0±0.2 g/dl in the control group. Fru was significantly lower in the administered group in 8 weeks than in the control group, as shown in FIG. 8, and the difference was more significant in 14 weeks (239±16 μmol/L in the administered group and 267±26 μmol/L in the control group).

Incidentally, during the test period there was no difference in body weight, amount of water taken and amount of food taken, between the two groups. Between the two groups there was no difference, either, in blood sugar in hungry state.

The above results indicate that the organogermanium compound (1-1) suppressed the glycation of proteins in plasma.

EXAMPLE 5

Streptozocin was intravenously injected into Sprague-Dawley female rats (total 21 rats each weighing 240–270 g) in an amount of 65 mg per kg of body weight to cause diabetes. Then, the rats were divided into two groups, i.e. a control group and an administered group. An organogermanium compound (1-1) was put into drinking water and orally administered to the administered group at night in an amount of 100 mg per kg of body weight.

14 weeks after the administration of the organogermanium compound (1-1), all the rats were killed to collect the skin of abdomen and the tendon of tail. Collagen was extracted from each skin and each tendon and treated with collagenase for solubilization. Each of the solubilized collagens was measured for fluorescence at an excitation wavelength of 370 nm and an absorption wave length of 440 nm. At the same time, hydroxyproline was measured by HPLC; a collagen amount was calculated; and the adjustment of fluorescent intensity was made using the value.

Figure 9:
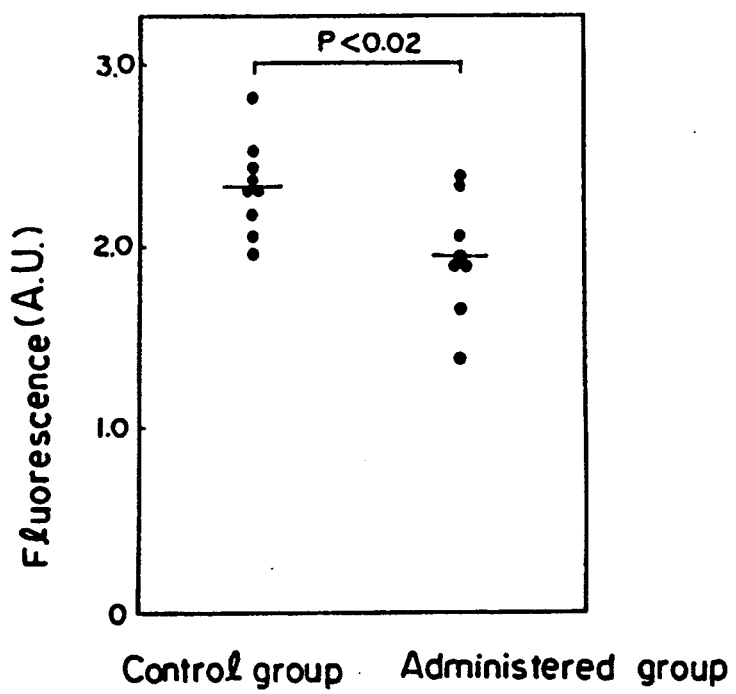
FIG. 9 is a graph showing that the present agent reduces the fluorescence of abdomen skin collagen in rats.
Figure 10:
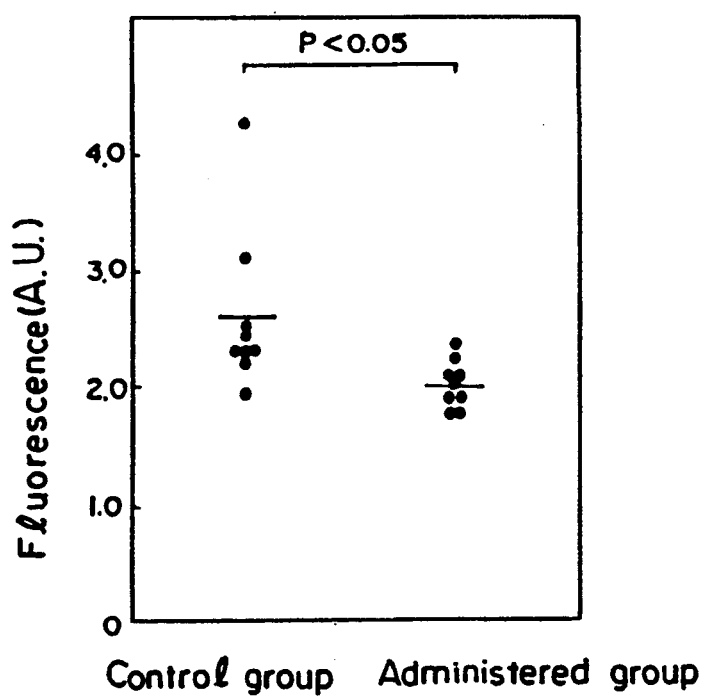
FIG. 10 is a graph showing that the present agent reduces the fluorescence of tail tendon collagen in rats.

As shown in FIG. 9, the fluorescence of skin collagen was 1.95±0.29 (arbitrary unit per mg of collagen, mean±SD) in the administered group and was significantly lower than 2.32±0.24 of the control group. As seen in FIG. 10, the fluorescence of tendon collagen was 2.01±0.18 in the administered group and was also significantly lower than 2.59±0.69 of the control group.

Incidentally, during the test period, i.e. 4, 8 and 14 weeks after the administration of the organogermanium compound (1-1), there was no difference in blood sugar in hungry state, body weight, amount of water taken and amount of food taken, between the two groups.

It is believed that the glycation of a protein having a low metabolism rate in living bodies, such as collagen or the like gives a crosslinked product at the later stage of the Mailard reaction and this is one cause for aging and complications of diabetes. The above results indicate that the organogermanium compound (1-1) suppressed the glycation of skin and tendon collagens.

EXAMPLE 6

An organogermanium compound (1-1) was administered to 20 diabetes patients (they were diagnosed as diabetes by a 75-g grape sugar loading test) at a dose of 750 mg/day for 2 months. Fructosamine content in serum of each patient was measured before and after the administration.

Fructosamine content in serum was measured by an ordinary method, i.e. by adding a test sample or a reference (a standard Amadori rearrangement product) to a NTB solution, subjecting the mixture to incubation at 37° C., and measuring the developed color.

Figure 11:
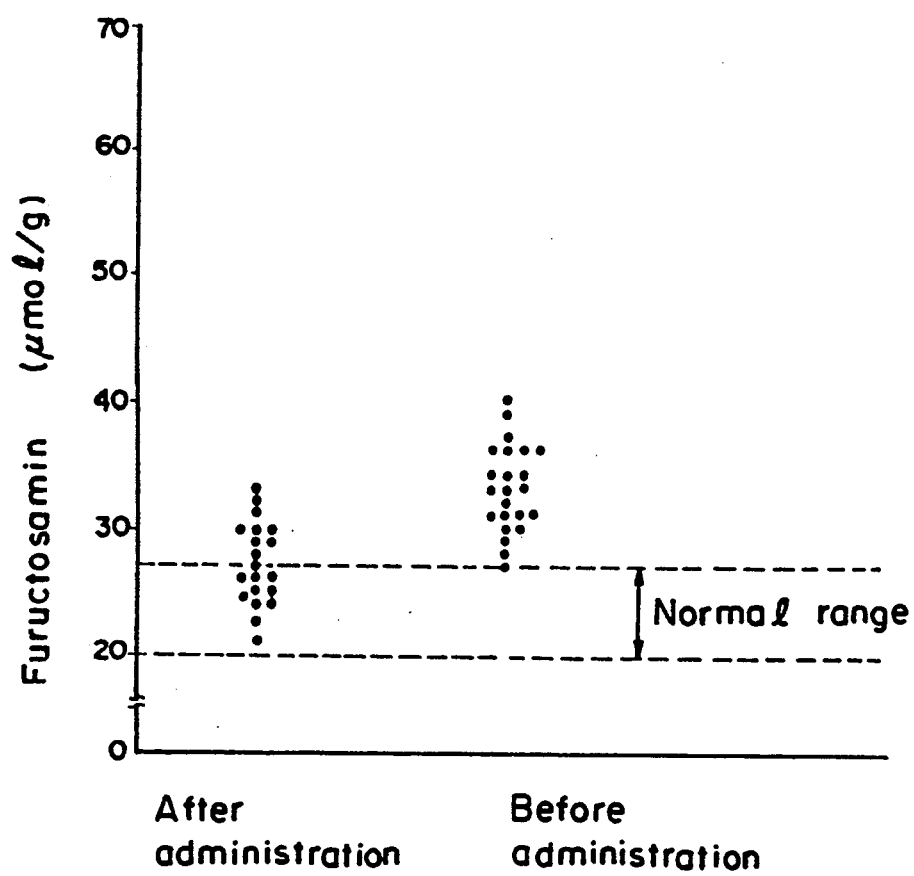
FIG. 11 is a graph showing that the present agent reduces serum Fructoamine in diabetes patients.

The results are shown in FIG. 11. As is clear from FIG. 11, the Fructosamine content in serum in diabetes patients was lower after the administration of the organogermanium compound (1-1) than before the administration.

The present agent comprises an organogermanium compound represented by formula (1) as the active component, and can effectively suppress or intercept the Mailard reaction both at the initial stage and at the later stage. Therefore, the present agent, when administered to living bodies, is effective for keto acidosis, infectious diseases, retinopathy, nephropathy, neuropathy, cerebrovascular disease, other complications of diabetes, etc.

Unlike the aminoguanidine or the like, the organogermanium compound (1) produces no protein unexperienced to human bodies, in living bodies because it has no functional group reactive with Amadori rearrangement products.

Further, the organogermanium compound (1) shows no side effect when administered and has very high safety. Therefore, even when administered for a long period of time for the treatment of, for example, complications of diabetes, the compound has very low possibility of giving an adverse effect to human bodies.

Complications of diabetes appear generally in about 10 years after a patient has been diagnosed as diabetes. Therefore, by starting the administration of the present agent after a patient has been diagnosed as diabetes, the manifestation of the complications can be suppressed or retarded. Hence, the present agent is expected to be also effective for prevention of complications of diabetes.

What is claimed is:

1. A method for suppressing or intercepting the Mailard reaction, which comprises administering an effective amount of an organogermanium compound represented by formula (1):

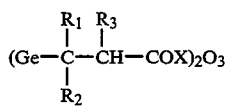

(1)

wherein $R_1$ to $R_3$ may be the same or different and each of them represents a hydrogen atom, a lower alkyl group, or a phenyl group; and X represents a hydroxyl group, an O-lower alkyl group, an amino group, or a salt represented by OY, wherein Y is an alkaline metal or a basic group-containing compound.

2. A method for suppressing or intercepting the Mailard reaction according to claim 1, wherein the organogermanium compound is a compound of formula (1) wherein each of $R_1$ to $R_3$ is a hydrogen atom and X is a hydroxyl group.

3. A method for suppressing or intercepting the Mailard reaction, which comprises administering an effective amount of an organogermanium compound represented by formula (2):

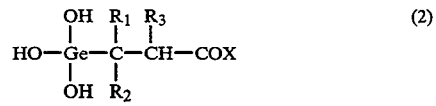

(2)

wherein $R_1$ to $R_3$ may be the same or different and each of them represents a hydrogen atom, a lower alkyl group, or a phenyl group; and X represents a hydroxyl group, an O-lower alkyl group, an amino group, or a salt represented by OY, wherein Y is an alkaline metal or a basic group-containing compound.

4. A method according to claim 3 wherein X is a hydroxyl group.

5. The method according to claim 1 wherein Y is sodium or potassium.

6. The method according to claim 3 wherein Y is sodium or potassium.

7. The method according to claim 1 wherein Y is lysozyme or lysine.

8. The method according to claim 3 wherein Y is lysozyme or lysine.

9. A method according to claim 1 wherein between about 5 and about 500 mg of the organogermanium compound is administered.

10. A method according to claim 3 wherein between about 5 and about 500 mg of the organogermanium compound is administered.

* * * * *